(12) United States Patent
Kwon et al.

(10) Patent No.: US 11,884,935 B2
(45) Date of Patent: Jan. 30, 2024

(54) METHOD FOR INDUCING TRANS-DIFFERENTIATION OF CARDIOMYOCYTES BASED ON EXOSOME

(71) Applicant: KOREA INSTITUTE OF SCIENCE AND TECHNOLOGY, Seoul (KR)

(72) Inventors: Ick Chan Kwon, Seoul (KR); Sun Hwa Kim, Seoul (KR); Yoosoo Yang, Seoul (KR); Hyosuk Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 483 days.

(21) Appl. No.: 16/456,127

(22) Filed: Jun. 28, 2019

(65) Prior Publication Data
US 2020/0002677 A1 Jan. 2, 2020

(30) Foreign Application Priority Data
Jun. 28, 2018 (KR) .......................... 10-2018-0074648

(51) Int. Cl.
*C12N 5/077* (2010.01)

(52) U.S. Cl.
CPC ........ *C12N 5/0657* (2013.01); *C12N 2500/30* (2013.01); *C12N 2500/32* (2013.01); *C12N 2500/38* (2013.01); *C12N 2501/235* (2013.01); *C12N 2501/33* (2013.01); *C12N 2506/02* (2013.01)

(58) Field of Classification Search
CPC .............. C12N 5/0657; C12N 2500/30; C12N 2500/32; C12N 2500/38; C12N 2501/235; C12N 2501/33; C12N 2506/02; C12N 2506/1307
See application file for complete search history.

(56) References Cited

U.S. PATENT DOCUMENTS

| 2013/0005796 A1 | 1/2013 | Kawashimi et al. |
| 2013/0280809 A1 | 10/2013 | Efe et al. |
| 2015/0315541 A1* | 11/2015 | Bancel ................. C12N 9/0069 435/366 |
| 2016/0251624 A1* | 9/2016 | Wang ................... C12N 5/0657 424/93.7 |
| 2017/0071937 A1* | 3/2017 | Karp ...................... A61K 31/167 |
| 2017/0304368 A1* | 10/2017 | Marban ................ C12N 5/0657 |

FOREIGN PATENT DOCUMENTS

KR 10-2013-0008560 A 1/2013
KR 10-2017-0106149-AA 9/2017

OTHER PUBLICATIONS

Singh et al ("Mechanism of Induction: Induced Pluripotent Stem Cells (iPSCs)," Journal of Stem Cells, 10(1), Jun. 2015) (Singh).*
Qin et al ("A narrative review of exosomes in vascular calcification," Ann Transl Med 2021; 9(7):579-591).*
Mor et al ("Species-specific microRNA regulation influences phenotypic variability," Bioessays 35: 881-888,(2013) (Year: 2013).*
Tseliou et al., "Exosomes from cardiac stem cells amplify their own bioactivity by converting fibroblasts to therapeutic cells," J. Am. Coll. Cardiol. (Aug. 11, 2015), vol. 66, No. 6, pp. 599-611.

* cited by examiner

*Primary Examiner* — Anoop K Singh
*Assistant Examiner* — Suzanne E Ziska
(74) *Attorney, Agent, or Firm* — Birch, Stewart, Kolasch & Birch, LLP

(57) ABSTRACT

The present invention relates to a method for inducing trans-differentiation of cardiomyocytes based on exosome, and more particularly, to a method for inducing trans-differentiation of a fibroblast into a cardiomyocyte, comprising the steps of: isolating exosomes in a culture medium during a process of differentiating a stem cell into the cardiomyocyte; culturing a fibroblast in a cardiomyocyte reprogramming medium containing the isolated exosomes; and culturing the fibroblast cultured in a cardiomyocyte differentiation medium containing the isolated exosomes.

8 Claims, 12 Drawing Sheets
Specification includes a Sequence Listing.

FIG. 3

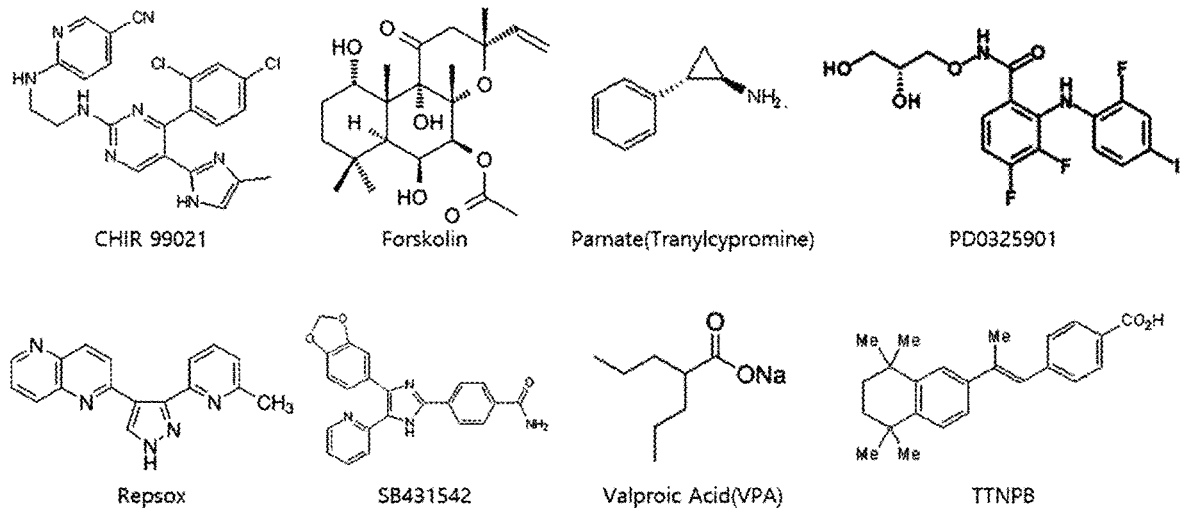

FIG. 4

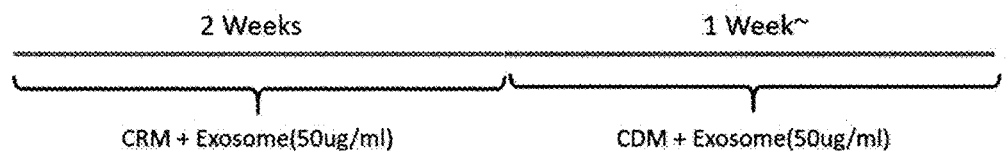

CRM : Cardiac Reprogamming Media
-Knock out DMEM
-Knockout Serum Replacement(5%)
-ES-FBS(15%)
-N2(0.5%), B27(2%)
-Glutamax(1%), NEAA(1%)
-β-mercaptoethanol(0.1mM)
-Ascorbic acid(50μg/ml)
-CRFVPT(Chemical cocktails) or SCPF(Chemical cocktails)

CDM : Chemically Defined Media for cardiomyocyte
-DMEM
-FBS(15%)
-Ascorbic acid(50μg/ml)
-Insulin(1μg/ml)
-LIF(1000 units/ml)
-CHIR99021(3μM)
-PD0325901(1μM)

SB431542
CHIR99021
Parnate(Tranylcypromine)
Forskolin
Repsox
TTNPB
Valproic Acid(VPA)
PD0325901

FIG. 5
Observation of morphology
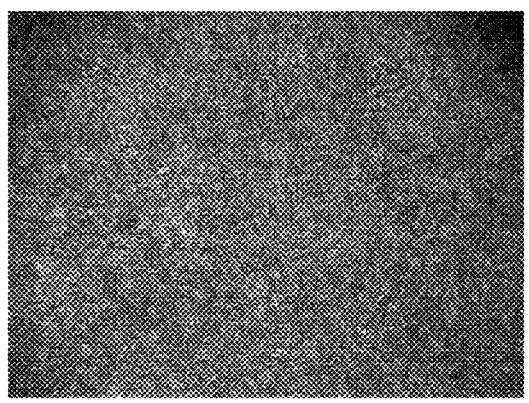
DAY1
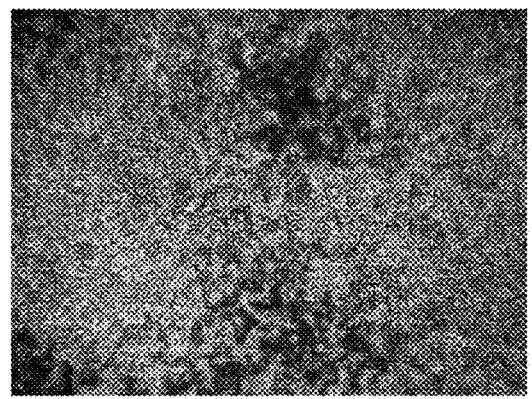
DAY5
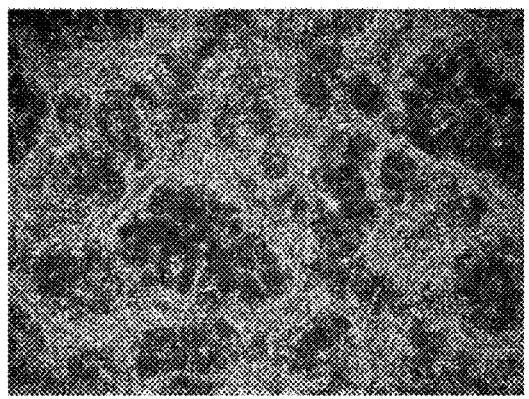
DAY10
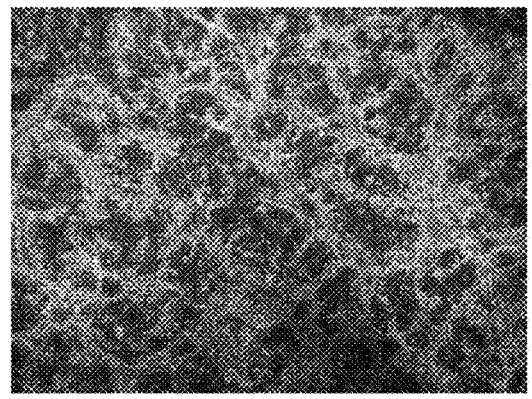
DAY15

FIG. 13
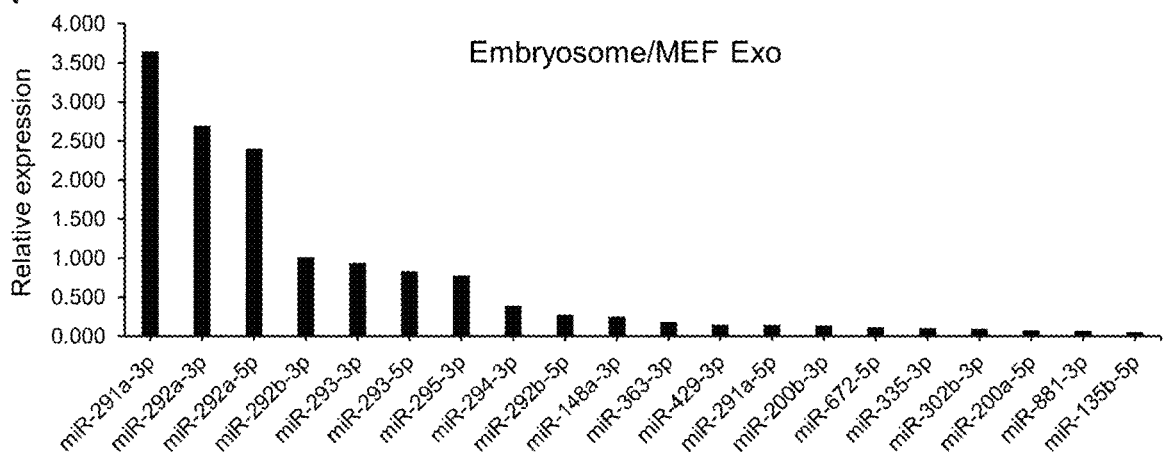
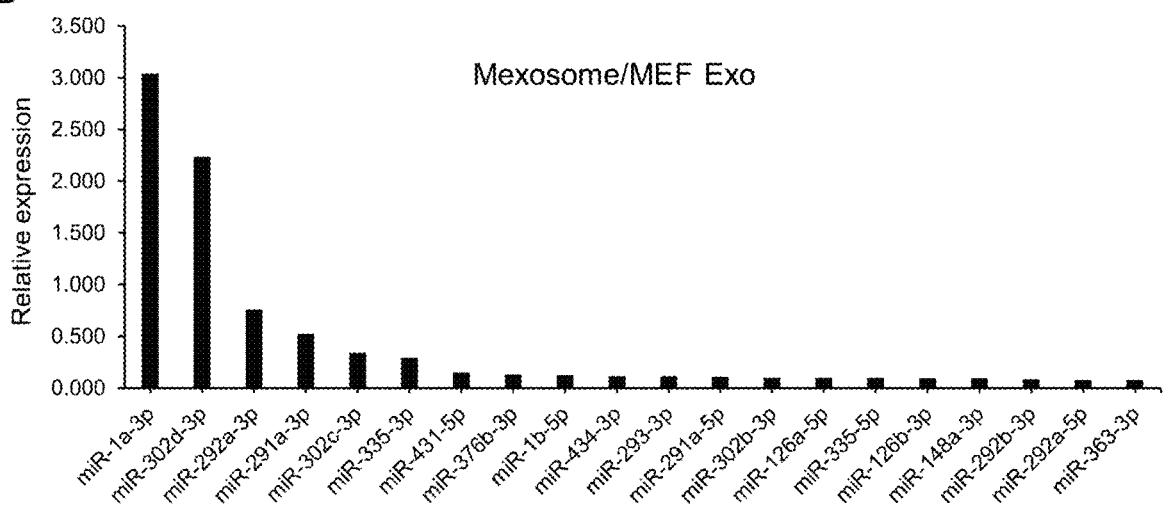

SEQUENCE LISTING

```
<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: Forward primer for Acta2

<400> SEQUENCE: 1
gtcccagaca tcagggagta a                                              21

<210> SEQ ID NO 2
<211> LENGTH: 21
<212> TYPE: DNA
<213> ORGANISM: Artificial Sequence
<220> FEATURE:
<223> OTHER INFORMATION: Reverse primer for Acta2

<400> SEQUENCE: 2
tcggatactt cagcgtcagg a                                              21

<210> SEQ ID NO 3
<211> LENGTH: 20
<212> TYPE: DNA
<213> ORGANISM: Artificial Sequence
<220> FEATURE:
<223> OTHER INFORMATION: Forward primer for CD31

<400> SEQUENCE: 3
ccgaagcagc actcttgcag                                                20

<210> SEQ ID NO 4
<211> LENGTH: 24
<212> TYPE: DNA
<213> ORGANISM: Artificial Sequence
<220> FEATURE:
<223> OTHER INFORMATION: Reverse primer for CD31

<400> SEQUENCE: 4
ctgcaactat taaggtggcg atga                                           24

<210> SEQ ID NO 5
<211> LENGTH: 20
<212> TYPE: DNA
<213> ORGANISM: Artificial Sequence
<220> FEATURE:
<223> OTHER INFORMATION: Forward primer for CNN2

<400> SEQUENCE: 5
ttcgagagcg ggaacatgac                                                20

<210> SEQ ID NO 6
<211> LENGTH: 21
<212> TYPE: DNA
<213> ORGANISM: Artificial Sequence
<220> FEATURE:
<223> OTHER INFORMATION: Reverse primer for CNN2

<400> SEQUENCE: 6
caatgaaaac cccaaagccc a                                              21

<210> SEQ ID NO 7
<211> LENGTH: 23
<212> TYPE: DNA
<213> ORGANISM: Artificial Sequence
```

```
<220> FEATURE:
<223> OTHER INFORMATION: Forward primer for Flk1

<400> SEQUENCE: 7
tttggcaaat acaacccttc aga                                            23

<210> SEQ ID NO 8
<211> LENGTH: 21
<212> TYPE: DNA
<213> ORGANISM: Artificial Sequence
<220> FEATURE:
<223> OTHER INFORMATION: Reverse primer for Flk1

<400> SEQUENCE: 8
gcagaagata ctgtcaccac c                                              21

<210> SEQ ID NO 9
<211> LENGTH: 21
<212> TYPE: DNA
<213> ORGANISM: Artificial Sequence
<220> FEATURE:
<223> OTHER INFORMATION: Forward primer for Gata4

<400> SEQUENCE: 9
cctggaagac accccaatct c                                              21

<210> SEQ ID NO 10
<211> LENGTH: 21
<212> TYPE: DNA
<213> ORGANISM: Artificial Sequence
<220> FEATURE:
<223> OTHER INFORMATION: Reverse primer for Gata4

<400> SEQUENCE: 10
aggtagtgtc ccgtcccatc t                                              21

<210> SEQ ID NO 11
<211> LENGTH: 24
<212> TYPE: DNA
<213> ORGANISM: Artificial Sequence
<220> FEATURE:
<223> OTHER INFORMATION: Forward primer for Isl1

<400> SEQUENCE: 11
agatcagcct gcctgctttt cagc                                           24

<210> SEQ ID NO 12
<211> LENGTH: 20
<212> TYPE: DNA
<213> ORGANISM: Artificial Sequence
<220> FEATURE:
<223> OTHER INFORMATION: Reverse primer for Isl1

<400> SEQUENCE: 12
aggactggct accatgctgt                                                20

<210> SEQ ID NO 13
<211> LENGTH: 21
<212> TYPE: DNA
<213> ORGANISM: Artificial Sequence
<220> FEATURE:
<223> OTHER INFORMATION: Forward primer for Mesp1

<400> SEQUENCE: 13
gtcactcggt cctggtttaa g                                              21
```

<210> SEQ ID NO 14
<211> LENGTH: 20
<212> TYPE: DNA
<213> ORGANISM: Artificial Sequence
<220> FEATURE:
<223> OTHER INFORMATION: Reverse primer for Mesp1

<400> SEQUENCE: 14
acgatgggtc ccacgattct                                            20

<210> SEQ ID NO 15
<211> LENGTH: 21
<212> TYPE: DNA
<213> ORGANISM: Artificial Sequence
<220> FEATURE:
<223> OTHER INFORMATION: Forward primer for Myh11

<400> SEQUENCE: 15
catcctgacc ccacgtatca a                                          21

<210> SEQ ID NO 16
<211> LENGTH: 21
<212> TYPE: DNA
<213> ORGANISM: Artificial Sequence
<220> FEATURE:
<223> OTHER INFORMATION: Reverse primer for Myh11

<400> SEQUENCE: 16
atcggaaaag gcgctcatag g                                          21

<210> SEQ ID NO 17
<211> LENGTH: 21
<212> TYPE: DNA
<213> ORGANISM: Artificial Sequence
<220> FEATURE:
<223> OTHER INFORMATION: Forward primer for Nanog

<400> SEQUENCE: 17
tcttcctggt ccccacagtt t                                          21

<210> SEQ ID NO 18
<211> LENGTH: 23
<212> TYPE: DNA
<213> ORGANISM: Artificial Sequence
<220> FEATURE:
<223> OTHER INFORMATION: Reverse primer for Nanog

<400> SEQUENCE: 18
gcaagaatag ttctcgggat gaa                                        23

<210> SEQ ID NO 19
<211> LENGTH: 21
<212> TYPE: DNA
<213> ORGANISM: Artificial Sequence
<220> FEATURE:
<223> OTHER INFORMATION: Forward primer for Nkx2.5

<400> SEQUENCE: 19
ggtctcaatg cctatggcta c                                          21

<210> SEQ ID NO 20
<211> LENGTH: 21
<212> TYPE: DNA
<213> ORGANISM: Artificial Sequence
<220> FEATURE:
<223> OTHER INFORMATION: Reverse primer for Nkx2.5

```
<400> SEQUENCE: 20
gccaaagttc acgaagttgc t                                              21

<210> SEQ ID NO 21
<211> LENGTH: 21
<212> TYPE: DNA
<213> ORGANISM: Artificial Sequence
<220> FEATURE:
<223> OTHER INFORMATION: Forward primer for Rex1

<400> SEQUENCE: 21
ccctcgacag actgaccta a                                               21

<210> SEQ ID NO 22
<211> LENGTH: 22
<212> TYPE: DNA
<213> ORGANISM: Artificial Sequence
<220> FEATURE:
<223> OTHER INFORMATION: Reverse primer for Rex1

<400> SEQUENCE: 22
tcggggctaa tctcactttc at                                             22

<210> SEQ ID NO 23
<211> LENGTH: 22
<212> TYPE: DNA
<213> ORGANISM: Artificial Sequence
<220> FEATURE:
<223> OTHER INFORMATION: Forward primer for Ryr2

<400> SEQUENCE: 23
acatcatgtt ttaccgcctg ag                                             22

<210> SEQ ID NO 24
<211> LENGTH: 23
<212> TYPE: DNA
<213> ORGANISM: Artificial Sequence
<220> FEATURE:
<223> OTHER INFORMATION: Reverse primer for Ryr2

<400> SEQUENCE: 24
tttgtggtta ttgaactctg gct                                            23

<210> SEQ ID NO 25
<211> LENGTH: 25
<212> TYPE: DNA
<213> ORGANISM: Artificial Sequence
<220> FEATURE:
<223> OTHER INFORMATION: Forward primer for Tie2

<400> SEQUENCE: 25
tgcccagata ttggtgtcct taaac                                          25

<210> SEQ ID NO 26
<211> LENGTH: 19
<212> TYPE: DNA
<213> ORGANISM: Artificial Sequence
<220> FEATURE:
<223> OTHER INFORMATION: Reverse primer for Tie2

<400> SEQUENCE: 26
tccgcagggc agtcaattc                                                 19

<210> SEQ ID NO 27
```

```
<211> LENGTH: 21
<212> TYPE: DNA
<213> ORGANISM: Artificial Sequence
<220> FEATURE:
<223> OTHER INFORMATION: Forward primer for Tnnt2

<400> SEQUENCE: 27
gcggaagagt gggaagagac a                                              21

<210> SEQ ID NO 28
<211> LENGTH: 20
<212> TYPE: DNA
<213> ORGANISM: Artificial Sequence
<220> FEATURE:
<223> OTHER INFORMATION: Reverse primer for Tnnt2

<400> SEQUENCE: 28
ccacagctcc ttggccttct                                                20

<210> SEQ ID NO 29
<211> LENGTH: 21
<212> TYPE: DNA
<213> ORGANISM: Artificial Sequence
<220> FEATURE:
<223> OTHER INFORMATION: Forward primer for VE-cadherin

<400> SEQUENCE: 29
tggcttgtcg aatttgaagc a                                              21

<210> SEQ ID NO 30
<211> LENGTH: 25
<212> TYPE: DNA
<213> ORGANISM: Artificial Sequence
<220> FEATURE:
<223> OTHER INFORMATION: Reverse primer for VE-cadherin

<400> SEQUENCE: 30
tctggtgagt gggttagagg ctatc                                          25
```

METHOD FOR INDUCING TRANS-DIFFERENTIATION OF CARDIOMYOCYTES BASED ON EXOSOME

CROSS-REFERENCES TO RELATED APPLICATIONS

This application claims the benefit of and priority to Korean Patent Application No. 2018-0074648, filed on Jun. 28, 2018, which is incorporated herein by this reference in its entirety.

TECHNICAL FIELD

The present invention relates to a method for inducing trans-differentiation of myocardial cells, and more particularly, to a method for inducing trans-differentiation of myocardial cells based on exosome.

BACKGROUND OF THE INVENTION

Cardiomyocytes lose their cell division ability in vivo, so they are not replenished even though they are exposed to various stresses such as ischemia and myocarditis and necrosis occurs thereby. As a result, the remaining cardiomyocytes try to maintain their function through compensatory hypertrophy. However, if this state continues and exceeds the allowable range of myocardial tissue, the cardiomyocytes become more impoverished or even dye, and finally, myocardial dysfunction, namely heart failure occurs. Cardiopathy, including heart failure, is one of the leading causes of death worldwide, caused by loss of myocardial cells or dysfunction. Patients with heart disease have a very poor prognosis, a 5-year survival rate of only about 50%, and the ability to regenerate myocardial cells is very limited. As conventional medicines for treating heart disease, heart stimulants such as digitalis agent and xanthine agent to enhance myocardial contractility have been used contractility. However, these drugs are sometimes known to aggravate the condition when administered over a long period of time. In addition, although agents alleviating cardiac hypertrophy due to enhancing sympathetic nervous system or the renin-angiotensin system such as a beta-blocker or an ACE inhibitor have been used, they are merely symptomatic remedies and not capable of restoring heart tissue itself. Cardiac transplantation, on the other hand, is a fundamental therapy for severe heart failure, but its use as a general treatment method is limited due to problems such as lack of organ donors, medical ethics, physical or economic burden of patients.

On the other hand, exosomes contain various physiologically active substances as vesicles secreted by cells for intercellular information exchange. In particular, stem cell-derived exosomes have the ability to differentiate and regenerate target cells or tissues through various proteins and miRNAs, and thus it is known that they can be extended to the regeneration and treatment of various cells and tissues. In this regard, Korean Patent Publication No. 2013-0008560 discloses a method for proliferating myocardial cells using microRNA.

SUMMARY OF THE INVENTION

However, in the case of the prior art described above, most virus vectors are used to introduce a gene, so that there is a possibility that genetic variation may occur and thus posing a safety problem.

The present invention is to solve various problems including the above-mentioned problems, and it is an object of the present invention to provide a method of inducing trans-differentiation of cardiomyocytes which is a kind of direct reprogramming method based on stem cell-derived exosome whose safety is secured through a combination of a biocompatible non-viral exosome and a cardiomyocyte-inducing chemical compound. However, these problems are exemplary and do not limit the scope of the present invention.

In an aspect of the present invention, there is provided a method of inducing trans-differentiation a fibroblast to a cardiomyocyte, the method comprising:
  isolating exosomes in a culture medium during a process of differentiating a stem cell into the cardiomyocyte;
  culturing a fibroblast in a cardiomyocyte reprogramming medium containing the isolated exosomes; and
  culturing the fibroblast cultured in a cardiomyocyte differentiation medium containing the isolated exosomes.

In another aspect of the present invention, there is provided a method for trans-differentiating a fibroblast into a cardiomyocyte, comprising:
  isolating exosomes in a culture medium during a process of differentiating stem cells into cardiomyocytes;
  culturing the fibroblast in a cardiomyocyte reprogramming medium containing the isolated exosomes; and
  culturing the fibroblast in a cardiomyocyte differentiation medium containing the isolated exosomes and a chemical agent for inducing cardiomyocyte.

In another aspect of the present invention, there is provided a composition for inducing trans-differentiation of a fibroblast into a cardiomyocyte comprising exosomes isolated from stem cells and a chemical agent for inducing cardiomyocyte differentiation.

Effects of the Invention

According to one embodiment of the present invention as described above, the exosome-based induction of trans-differentiation of cardiomyocytes makes it possible to directly induce cardiomyocytes from somatic cells without intermediate step of preparing induced pluripotent stem cells (iPSCs) by introducing a cardiomyocyte inducing compound and exosomes derived from the stem cells into the somatic cells. Since it does not use a viral vector, it can secure safety in the body without worrying about genetic mutation due to viral infection. However, the scope of the present invention is not limited by these effects.

BRIEF DESCRIPTION OF DRAWINGS

FIG. 3 is a schematic diagram showing a chemical structure of a chemical agent for inducing cardiomyocytes of the present invention.

FIG. 4 is a schematic diagram showing a method for inducing cardiomyocytes using the chemical agent for inducing cardiomyocytes and exosomes derived from stem cells.

FIG. 5 is a series of photographs showing morphologies of cells from 0 to 15 days after treating a chemical agent for inducing and exosomes derived from stem cells to mouse embryonic fibroblasts at 5 day interval using an optical microscope.

FIG. 13 is a series of graphs showing comparison of relative expression levels of miRNAs in embryosome/MEF-exosome and mexosome/MEF-exosome. miRNA expression levels were calculated using read counts, and miRNAs with higher expression levels in embryosome (A) and mexosome (B) than MEF and ESC-derived exosomes were investigated. The expression levels of miR-290 cluster, miR-302-367 cluster, and miR-200, which are involved in pluripotency, mesoderm induction, and somatic reprogramming, respectively, were particularly high in embryosomes, and miR-1 playing an important role in cardiac development and function stood out as a highly elevated miRNA in mexosomes.

DETAILED DESCRIPTION OF THE INVENTION

Definitions

Figure 1:
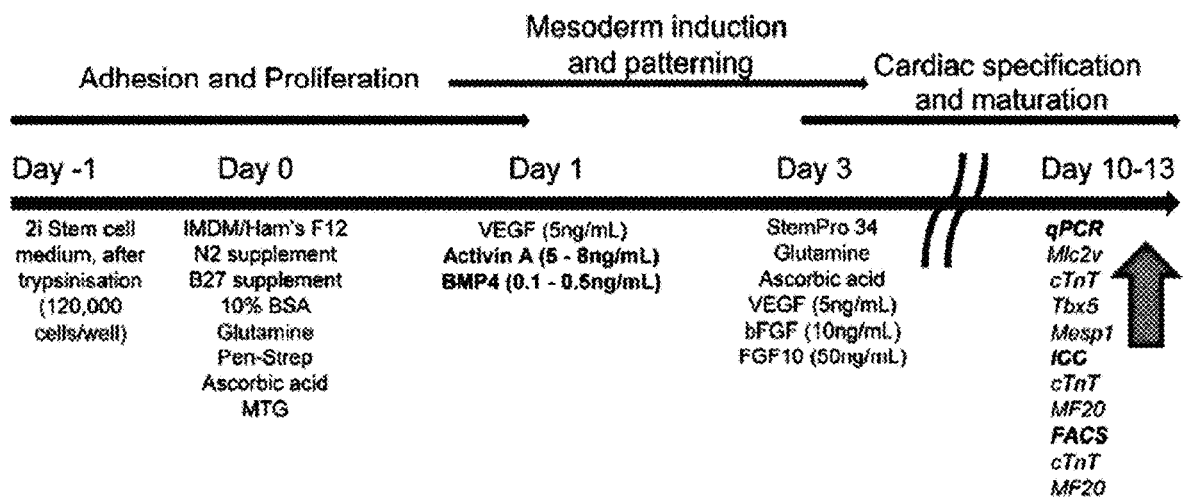
FIG. 1 is a schematic diagram showing a method of inducing cardiomyocytes from mouse embryonic stem cells (E14tg2a).

As used herein, the term "exosome" means a cell-derived vesicle that may be present in all biological fluids, including, perhaps, blood, urine, and cell culture medium and it is also called as "extracellular vesicle" or "microvesicle" alternatively. The size of the exosomes is known to be between 30 and 100 nm, and when the multivesicular body fuses with the cell membrane, it is secreted from the cell or secreted directly through the cell membrane. Exosomes are known to play an important role in a variety of processes such as clotting, intercellular signaling, and metabolic waste management.

As used herein, the term "embryosomes or mexosomes" means the exosomes obtained between the embryonic body (EB) formation stage and the stage before mesodermal induction or the mesodermal induction and heart maturation stages, respectively.

As used herein, the term "direct cell conversion technique" means a process that induces the conversion between mature (differentiated) cells with totally different cell types in higher organisms, which is a technique to directly trans-differentiate a finally differentiated somatic cell into another type of somatic cell by changing its destiny. Unlike the process of reprogramming the cells with inducible pluripotent stem cells (iPSCs) and redifferentiating them to produce the desired cells, it is possible to induce the conversion to the desired cell without preparing the inducible pluripotent stem cells. It is expected that direct trans-differentiation will be used for disease modeling and drug discovery, and it will be applied to gene therapy and regenerative medicine in the future. Recently, it has been reported that it is possible to reprogram fibroblast into various cells such as blood, blood vessels, muscles, etc. as well as organs such as the brain and heart, which is known to be impossible to regenerate, thus the possibility of use as a therapeutic agent for reprogrammed cells is increasing.

As used herein, the term "induced cardiomyocyte (iCM)" means a cardiomyocyte trans-differentiated from a fibroblast by treating with exosomes derived from stem cells and a chemical agent for inducing cardiomyocyte differentiation according to an embodiment of the present invention.

DETAILED DESCRIPTION OF THE INVENTION

In an aspect of the present invention, there is provided a method of inducing trans-differentiation a fibroblast to a cardiomyocyte, the method comprising:
    isolating exosomes in a culture medium during a process of differentiating a stem cell into the cardiomyocyte;
    culturing a fibroblast in a cardiomyocyte reprogramming medium containing the isolated exosomes; and
    culturing the fibroblast cultured in a cardiomyocyte differentiation medium containing the isolated exosomes.

According to the method, the exosomes may be prepared by mixing a first exosome isolated during a mesoderm induction process and a second exosome isolated during a cardiac specification and maturation process, and the mixing ratio of the first exosome and the second exosome may be from 1:19 to 19:1.

According to the method, the cardiomyocyte reprogramming medium comprises 2 to 7 wt % of KnockOut™ Serum Replacement, 10 to 17 wt % of embryonic stem cell fetal calf serum (ES-FBS), 0.1 wt % of N-2™, 1 to 3 wt % of B-27™, 0.5 to 2 wt % of Glutamax™, 0.5 to 2 wt % of nonessential amino acid (NEAA), 0.05 to 0.2 mM of β-mercaptoethanol, and 20 to 70 µg/ml of ascorbic acid.

According to the method, the cardiomyocyte differentiation medium may contain 12 to 20 wt % of fetal bovine serum, 20 to 70 µg/ml of ascorbic acid, 0.5 to 2 µg/ml of insulin, and 500 to 1,500 units/ml of leukemia inhibitory factor actor.

According to method, the cardiomyocyte differentiation medium may further comprise a chemical agent for inducing cardiomyocyte differentiation, and the chemical agent may be CHIR99021, PD0325901, SB431542, Parnate (Tranylcypromine), Forskolin, Repsox, TTNPB, and Valproic Acid (VPA), and the chemical agent may be added to the cardiomyocyte differentiation medium at a concentration of 1 to 50 µM.

The CHIR99021 is the most selective GSK3 inhibitor among WNT agonists reported to date which inhibits GSK3β ($IC_{50}$=6.7 nM) and GSK3α ($IC_{50}$=10 nM). It is also used to differentiate myocardial cells from human embryonic stem (ES) and induced pluripotent stem cells (iPSCs). PD0325901 is also used as an inhibitor of the MEK/ERK pathway that inhibits MEK activation and downstream signaling and is used in combination with CHIR99021 to maintain the undifferentiation state of mouse embryonic stem (ES) cells.

In another aspect of the present invention, there is provided a method for trans-differentiating a fibroblast into a cardiomyocyte, comprising:

isolating exosomes in a culture medium during a process of differentiating stem cells into cardiomyocytes;

culturing the fibroblast in a cardiomyocyte reprogramming medium containing the isolated exosomes; and culturing the fibroblast in a cardiomyocyte differentiation medium containing the isolated exosomes and a chemical agent for inducing cardiomyocyte.

According to the method, the exosomes may be prepared by mixing a first exosome isolated during a mesoderm induction process and a second exosome isolated during a cardiac specification and maturation process.

In another aspect of the present invention, there is provided a composition for inducing trans-differentiation of a fibroblast into a cardiomyocyte comprising exosomes isolated from stem cells and a chemical agent for inducing cardiomyocyte differentiation.

According to the composition, the exosomes may be prepared by mixing a first exosome isolated during a mesoderm induction process and a second exosome isolated during a cardiac specification and maturation process.

According to the composition, the chemical agent may be one or a mixture of two or more selected from the group consisting of CHIR99021, PD0325901, SB431542, Tranylcypromine, Forskolin, Repsox, TTNPB, and Valproic Acid (VPA).

In recent years, studies on cell-based cardiac therapy in which cardiomyocytes are obtained from induced pluripotent stem cells (iPSCs) are attracting attention, but when the iPSCs are used, the risk of forming a teratoma. Therefore, there are limitations in clinical application and it is time consuming because it is necessary to dedifferentiate somatic cells into inducible pluripotent stem cells and then redifferentiate them into myocardial cells, and there is a drawback that the conversion ratio is also very low. In addition, there are direct reprogramming methods for cell-based therapies that are presented as alternatives to the iPSCs. By introducing myocardial induction genes, or by introducing totipotent gens and then inhibiting a specific signal transduction pathway using a low molecular weight chemical at an intermediate stage before fully acquiring a totipotency, fibroblasts can be differentiated into myocardial cells.

On the other hand, exosomes are vesicles of 50-150 nm size, which are secreted by cells for intercellular information exchange, and contain various physiologically active substances. Since exosome contains intracellular proteins, cell membrane proteins, lipid, RNA, miRNA, DNA, and various factors related to cell differentiation, growth, migration and signal transduction, it has unlimited potential to be used as a carrier, especially for cell reprogramming factors. Furthermore, since exosome is a cell-derived substance with excellent biocompatibility and it is composed of a lipid bilayer like cells, it can deliver various active substances (drug, gene, and protein) safely and efficiently. However, it is difficult to reprogram cells in a specific direction due to various factors having various functions. In order to induce the behavior and destiny of cells in a desired direction, exosome engineering technology capable of specializing and strengthening specific functions is required. Accordingly, the present inventors have found that stem cell-derived exosomes are capable of differentiating and regenerating through various proteins and miRNAs as a result of studying the direct reprogramming method securing the safety through epigenetic manipulation. Further, it was found that the exosomes derived from stem cells including miRNAs and proteins which are related to myocardial cell induction, and chemical agents for inducing cardiomyocytes were delivered into other somatic cells such as fibroblasts efficiently and the somatic cells can be directly differentiated into myocardial cells without intermediate steps of preparing stem cells and its biosafety is superior to viral vectors. Form such findings, the present inventors established the exosome-based method of inducing trans-differentiation of myocardial cells according to the present invention was accomplished (FIG. 1).

BEST MODE FOR THE INVENTION

Hereinafter, the present invention will be described in more detail by following examples and experimental examples. It will be apparent to those skilled in the art that the present invention is not limited to the disclosed examples, but may be embodied in many different forms and the examples are provided in order to complete the disclosure of the present invention and to fully convey the scope of the invention to those skilled in the art.

Conventional Methods

Materials CHIR99021, Repsox, Forskolin, VPA, PD0325901, and SB431542 which are used for the present invention were purchased from Sigma-Aaldrich, and Glutamax™, N-2™, B-27™, NEAA, β-mercaptoethanol, ascorbic acid, KnockOut™ DMEM, KnockOut™ serum replacement and ES-FBS were purchased from Thermo Fisher Scientific Inc. In addition, Parnate and TTNPB were purchased from Tocris Bioscience, E14Tg2a cells were purchased from ATCC and MEF was purchased from Lonza.

Cardiac Reprogramming Culture (CRM)

The cardiac reprogramming medium of the present invention was prepared by knockout DMEM medium containing 5% of KnockOut™ Serum Replacement, 15% of ES-FBS, 0.5% of N-2™, 2% of B-27™, 1% of Glutamax™, 1% of non-essential amino acid (NEAA), 0.1 mM β-mercaptoethanol, and 50 μg/ml of ascorbic acid. The composition of the KnockOut™ Serum Replacement is summarized in Table 1 below.

TABLE 1

Constitution of KnockOut™ Serum Replacement

| Type of ingredients | Component |
|---|---|
| Amino acids | Glycine, L-histidine, L-isoleucine, L-methionine, L-phenylalanine, L-proline, L-hydroxyproline, L-serine, L-threonine, L-tryptophan, L-tyrosine, L-valine |
| Vitamins/ Antioxidants | thiamine, reduced glutathione, ascorbic acid 2-PO$_4$ |
| Trace Elements | $Ag^+$, $Al^{3+}$, $Ba^{2+}$, $Cd^{2+}$, $Co^{2+}$, $Cr^{3+}$, $Ge^{4+}$, $Br^-$, $I^-$, $F^-$, $Mn^{2+}$, $Si^{4+}$, $V^{5+}$, $Mo^{6+}$, $Ni^{2+}$, $Rb^+$, $Sn^{2+}$, and $Zr^{4+}$ |
| Proteins | transferrin(iron-saturated), insulin, lipid-rich albumin (AlbuMAX) |

Cardiac Differentiation Medium (CDM)

The cardiac differentiation medium of the present invention is prepared by adding 15% fetal bovine serum, 50 μg/ml ascorbic acid, 1 μg/ml insulin, leukemia inhibitory factor 1000 units/ml, and additionally, 3 μM of CHIR99021 and 1 μM of PD0325901 into DMEM.

Example 1: Extraction of Exosome

Figure 2:
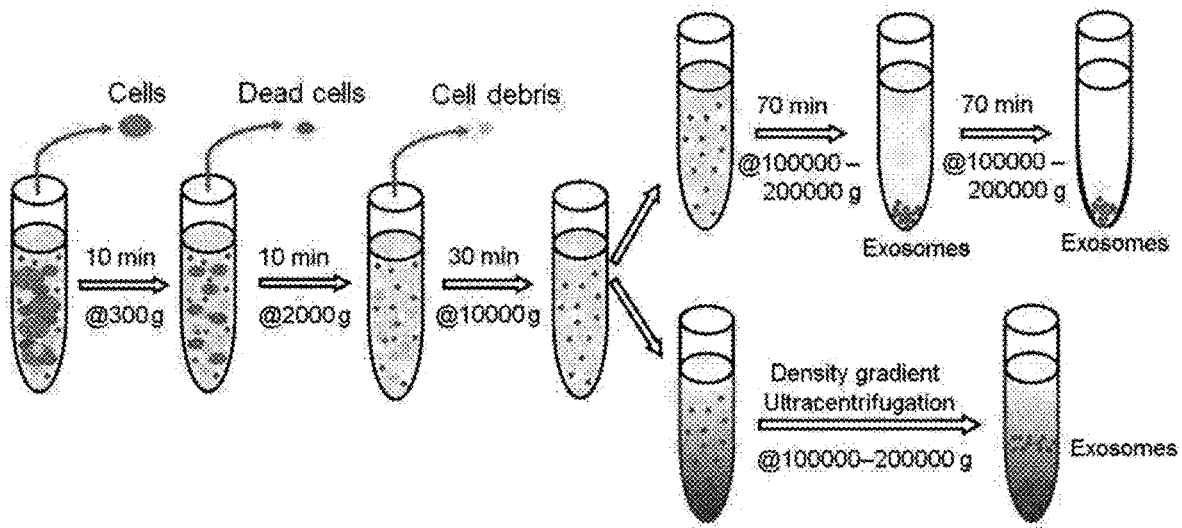
FIG. 2 is a schematic diagram showing a method of extracting stem cell-derived exosomes according to an embodiment of the present invention.

The present inventors extracted exosomes from the process of differentiating mouse embryonic stem cells (E14tg2a) into cardiomyocytes. Particularly, culture medium of cultivated mouse embryonic stem cells was all transferred to a tube and centrifuged for 10 minutes at 300 xg to separate the cells, and the dead cells were separated by centrifugation at 2,000×g for 10 minutes. Thereafter, cell debris and impurities were separated at 10,000 xg for 30 minutes. The separated medium whose cells, dead cells and cell debris were removed was further centrifuged was at 150,000 xg for 70 minutes using an ultracentrifuge. After removing supernatant, the mass of exosomes clinging to the bottom was resuspended with PBS. Finally, exosomes were extracted by ultracentrifugation at 150,000×g for 70 minutes (FIG. 2). The exosome extracted in the mesoderm induction process were called as a first exosome, and the exosome extracted in the cardiac specification and maturation process were called as a second exosome. The two types of exosomes were mixed at 5:5 and used in the following experiments.

Example 2: Direct Trans-Differentiation of Fibroblasts

The present inventors induced differentiation of mouse embryonic fibroblasts into cardiomyocytes by adding the extracted exosome and chemical agent for inducing cardiomyocyte differentiation to the mouse embryonic fibroblasts.

Specifically, mouse embryonic fibroblasts were seeded at a density of 50,000 cells/well in a 6-well plate coated with Matrigel®, cultured for 24 hours, and then further cultured for 1 week in a cardiac reprogramming media (CRM) containing the exosomes (50 μg/ml) prepared in Example 1. Thereafter, the fibroblasts were further cultured for 1 week in a cardiac differentiation media (CDM) containing exosomes (50 μg/ml) prepared in Example 1 (FIG. 4). In addition, a mixture of CHIR99021 and PD0325901 which was used as a chemical agent for inducing cardiomyocyte differentiation being added to the cardiomyocyte differentiation media. However, SB431542, Parnate (Tranylcypromine), Forskolin, Repsox, TTNPB and Valproic Acid (VPA) may be used as the chemical agent.

Example 3: Cell Morphology Analysis

The present inventors observed cell morphology after culturing fibroblasts in the cardiac reprogramming mediums (CRM). Specifically, mouse embryonic fibroblasts were cultured in DMEM supplemented with 10% FBS and 1% antibiotics at 37° C. for 24 hour. The cultured cells were seeded on a 6-well plate at a density of $5 \times 10^4$ cells/well and cultured for 24 hours. The culture medium was replaced with the CRM and the morphology of cells was observed with an optical microscope.

As a result, the mouse embryonic fibroblasts showed a proliferative pattern in the planar state before the replacement of the CRM, but they formed clusters in the form of lumps of cells over time after the medium replacement. In addition, in the medium-replaced mouse fibroblast group, multinucleated cells having 2-3 nuclei were observed, and the rate of cell proliferation was remarkably decreased. When the cells were further cultured in the CDM, cells beating spontaneously were also observed (FIG. 5). These morphological changes suggest that the cell type has been changed.

Example 4: Immunocytochemical Analysis

The present inventors performed immunocytochemical analysis to confirm direct reprogramming from fibroblasts to cardiomyocytes. Specifically, mouse embryonic fibroblasts were seeded on a 6-well plate at a density of $5 \times 10^4$ cells/well, and then cultured for 24 hours. Subsequently, the culture medium was replaced with a cardiac reprogramming medium (CRM) and cultured for 2 weeks. And then, the culture medium was replaced with a cardiac differentiation medium (CDM), and further cultivation was performed for 1 week. For immunostaining, the cells obtained through the above culturing process were treated with trypsin, transferred to a 35 mm glass bottom culture dish, and settled to adhere to the bottom of the culture dish.

The induced cardiomyocytes (iCMs) were washed twice with Dulbecco's phosphate-buffered saline (DPBS), treated with 0.25% Trypsin/EDTA (Thermo Scientific) and incubated at 37° C. for 2 minutes. The cells were resuspended gently three times with a P1000 pipette, incubated for another 2 min at 37° C., and then placed in the same volume of 4° C. 10% FBS-PBS, gently mixed twice and pelleted at 125 xg for 3 minutes. The induced cardiomyocytes (iCMs) were plated on a glass bottom dish (Nunc) coated with 0.1% gelatin type A (Sigma-Aldrich) and grown for two more days. Cells were fixed with 4% paraformaldehyde (Sigma-Aldrigh) for 15 minutes at room temperature and permeabilized with 0.1% Triton X-100 (Sigma Aldrich) for 10 minutes at room temperature. Subsequently, cells were blocked with 5% BSA for 1 hour at room temperature, and stained with anti-alpha-MHC mouse IgG (ab50967, Abcam, 1:200), anti-cTnT mouse IgG (ab8295, Abcam, 1:200), anti-cTnI rabbit IgG (ab47003, Abcam, 1:100), anti-Gata4 rabbit IgG (ab84593, Abcam, 1:200), anti-Mef2c rabbit IgG (ab64644, Abcam, 1:200), anti-Nkx-2.5 mouse IgG (ab91196, Abcam, 1:200), anti-Connexin-43 rabbit IgG (ab11370, Abcam, 1:200), polyclonal rabbit IgG polyclonal anti-MLC2v rabbit IgG (ab79935, Abcam, 1:200), monoclonal anti-Ki67 mouse IgG (ab8191, Abcam, 1:200), monoclonal anti-α-actinin rabbit IgG (7H1L69, Thermo Fisher Scientific, 1:100), monoclonal anti-MLC2a mouse IgG (#311011, Synaptic systems, 1:300), polyclonal anti-Is11 rabbit IgG (LS-C334676, LifeSpan BioSciences, 1:100), monoclonal anti-SMA mouse IgG (A2547, Sigma Aldrich, 1:400), polyclonal anti-Calponin 2 goat IgG (sc-16607, Santa Cruz, 1:100), polyclonal anti-PECAM goat IgG (sc-1506, Santa Cruz, 1:100), or monoclonal anti-VE-cadherin mouse IgG (sc-9989, Santa Cruz, 1:100) overnight at 4° C. in 1% BSA in DPBS. Cells were washed twice with 1% BSA in DPBST for 15 minutes and then incubated for 1 hour at room temperature in the dark with secondary antibodies 1:2000 Alexa Fluor™ 488 goat anti-mouse IgG (H&L), 1:2000 Alexa Fluor™ 488 donkey anti-rabbit IgG (H&L), 1:2000 Alexa Fluor™ 647 goat anti-mouse IgG (H&L), 1:2000 Alexa Fluor™ 647 donkey anti-rabbit IgG (H&L), 1:2000 Alexa Fluor™ 488 donkey anti-goat IgG (H&L), or 1:2000 Alexa Fluor 647 donkey anti-goat IgG (H&L) (all from Life Technologies) in 1% BSA in DPBS. Cells were washed again as above, nuclei were stained with DAPI (4,6-diamidino-2-phenylindole, Sigma Aldrich), and imaged with a TCS SP5 confocal microscope (Leica Microsystems).

Figure 6:
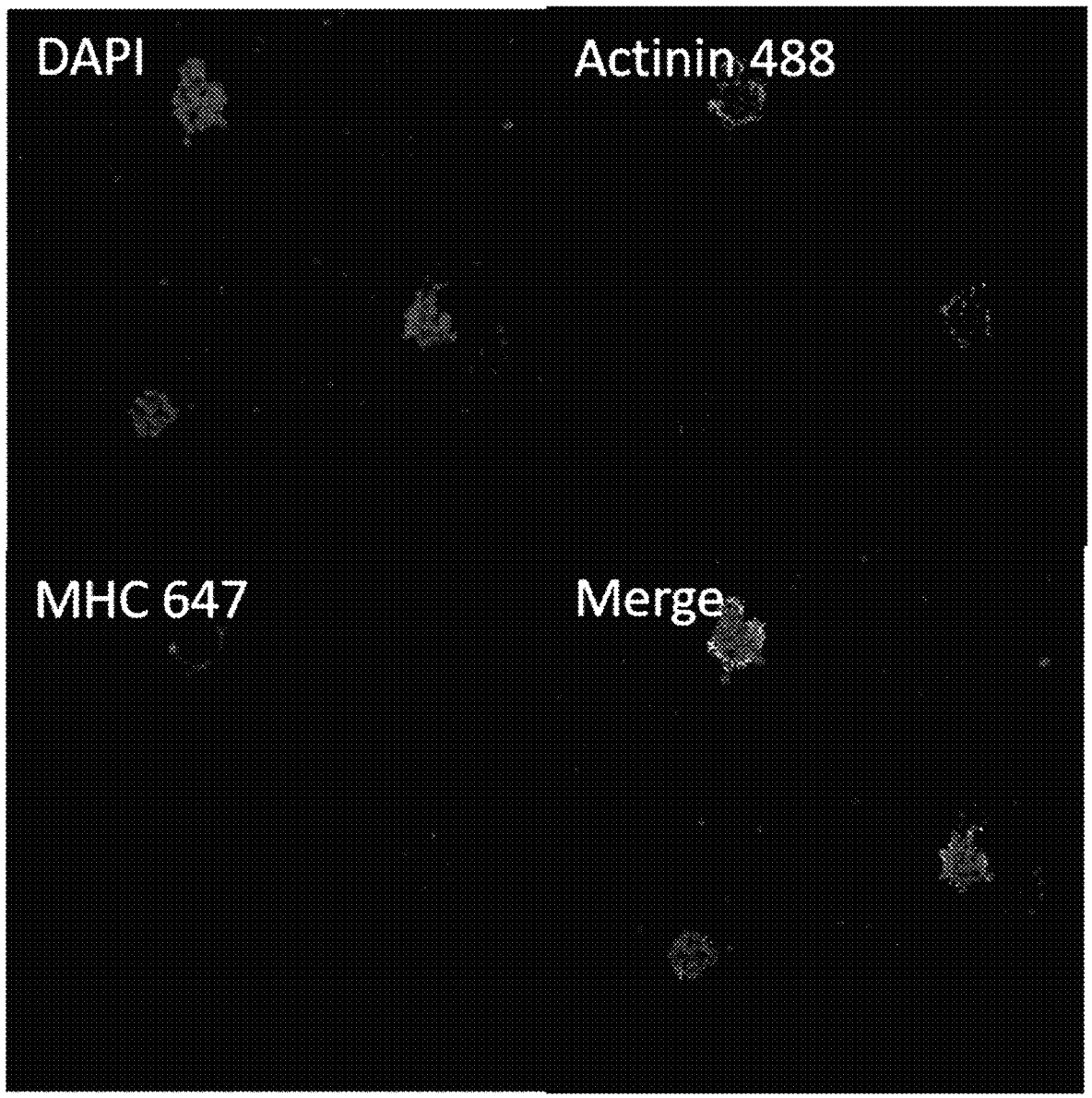
FIG. 6 is series of photographs showing results of fluorescence immunocytochemical analysis on fibroblast treated with a chemical agent for inducing cardiomyocyte and exosomes derived from stem cells and stained with fluorescent dye-conjugated anti-α-actinin and anti-α-myosin heavy chain (α-MHC) antibodies, respectively, in order to identify direct reprogramming into cardiomyocytes.
Figure 7:
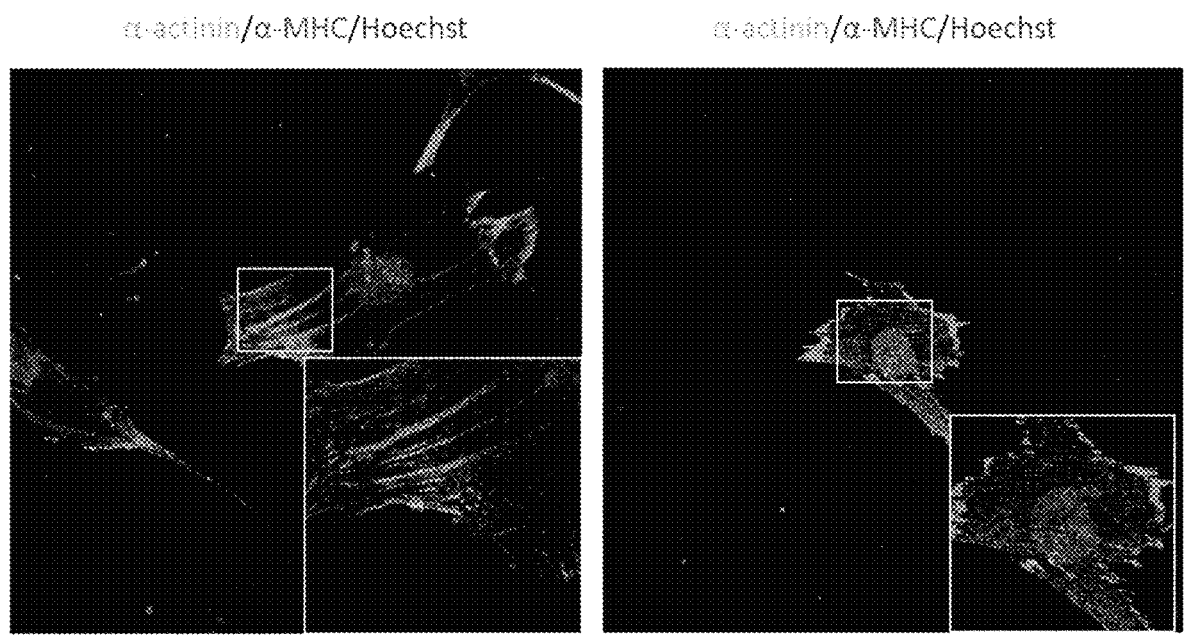
FIG. 7 is a series of photographs showing fluorescence immunocytochemical analysis on single-celled cardiomyocytes isolated from a lump of cardiomyocytes prepared by treating fibroblasts with a chemical agent for inducing cardiomyocyte and exosomes derived from stem cells, which beats after stained with fluorescent dye-conjugated anti-α-actinin and anti-α-myosin heavy chain (α-MHC) antibodies, respectively, in order to examine the morphology of sarcomere which is a characteristic of myocardial cells.

As a result, the expression of α-actinin and α-MHC, which are myocardial specific markers, was observed in mouse embryonic fibroblasts treated with the CRM and CDM (FIG. 6). In addition, some sarcomere structures commonly observed in the myocardium were observed in some of the mouse embryonic fibroblasts (FIG. 7).

Figure 8:
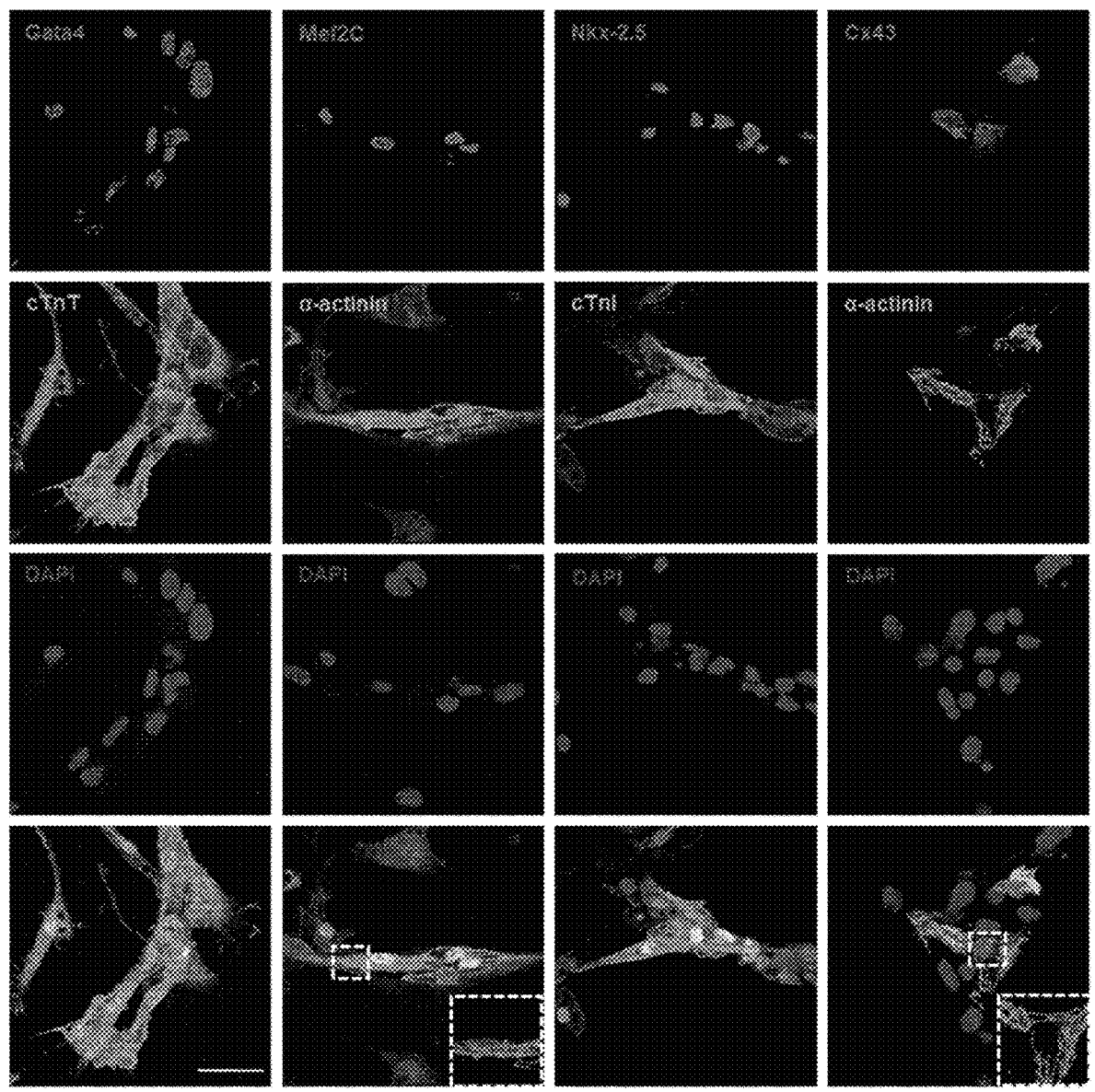
FIG. 8 is a series of photographs showing immunofluorescent staining on induced cardiomyocytes (iCM) prepared by treating fibroblasts with exosome derived from stem cells and a chemical agent for inducing cardiomyocyte differentiation using antibodies against various cardiomyocyte-specific proteins in order to analyze the expression of cardiomyocyte-specific genes.

Further, immunofluorescent staining demonstrated that Gata4, Mef2C, and NkX2.5, which are late cardiac cell markers and important transcription factors for cardiac development, were highly expressed in iCMs, and connexin43 (cx43), one of the components of gap junctions for intercellular communication, was also expressed (FIG. 8).

Example 5: Quantitative Real-Time PCR

The present inventors observed the expression of mouse cardiomyocyte-specific genes in cardiomyocytes trans-differentiated from mouse embryonic fibroblasts. Specifically, cells were dissociated with TrypLE™ Express reagent (Thermo Scientific), and pellets were stored in a deep-freezer at −80° C. Total RNA from samples at designated time points was extracted using an RNeasy Plus mini kit with QiaShredder™ (QIAGEN), RNA was reverse-transcribed using a High Capacity RNA-to-cDNA kit (Life Technologies), and quantitative real-time PCR was performed with PowerUp™ SYBR™ Green Master Mix (Thermo Scientific) on the StepOnePlus™ Real-Time PCR System (Applied Biosystems). The real time PCR was performed for 1 cycle at 50° C. for 2 minutes and 1 cycle at 95° C. for 10 minutes, followed by 40 cycles of 95° C. for 15 seconds, 60° C. for 30 seconds, and 72° C. for 30 seconds. Additional extension reaction was performed with 1 cycle at 72° C. for 10 minutes to complete the amplification. The nucleic acid sequences of the primers used in the real time PCR are summarized in Table 2 below.

TABLE 2

Primer Information for real time PCR

| Target | Primer | Nucleotide Sequences (5'→3') | SEQ ID NO |
|---|---|---|---|
| Acta2 | F | GTCCCAGACATCAGGGAGTAA | 1 |
| Acta2 | R | TCGGATACTTCAGCGTCAGGA | 2 |
| CD31 | F | CCGAAGCAGCACTCTTGCAG | 3 |
| CD31 | R | CTGCAACTATTAAGGTGGCGATGA | 4 |
| CNN2 | F | TTCGAGAGCGGGAACATGAC | 5 |
| CNN2 | R | CAATGAAAACCCCAAAGCCCA | 6 |
| Flk1 | F | TTTGGCAAATACAACCCTTCAGA | 7 |
| Flk1 | R | GCAGAAGATACTGTCACCACC | 8 |
| Gata4 | F | CCTGGAAGACACCCCAATCTC | 9 |
| Gata4 | R | AGGTAGTGTCCCGTCCCATCT | 10 |
| Isl1 | F | AGATCAGCCTGCCTGCTTTTCAGC | 11 |
| Isl1 | R | AGGACTGGCTACCATGCTGT | 12 |
| Mesp1 | F | GTCACTCGGTCCTGGTTTAAG | 13 |
| Mesp1 | R | ACGATGGGTCCCACGATTCT | 14 |
| Myh11 | F | CATCCTGACCCCACGTATCAA | 15 |
| Myh11 | R | ATCGGAAAAGGCGCTCATAGG | 16 |
| Nanog | F | TCTTCCTGGTCCCCACAGTTT | 17 |
| Nanog | R | GCAAGAATAGTTCTCGGGATGAA | 18 |
| Nkx2.5 | F | GGTCTCAATGCCTATGGCTAC | 19 |
| Nkx2.5 | R | GCCAAAGTTCACGAAGTTGCT | 20 |
| Rex1 | F | CCCTCGACAGACTGACCCTAA | 21 |
| Rex1 | R | TCGGGGCTAATCTCACTTTCAT | 22 |
| Ryr2 | F | ACATCATGITTTACCGCCTGAG | 23 |
| Ryr2 | R | TTTGTGGTTATTGAACTCTGGCT | 24 |
| Tie2 | F | TGCCCAGATATTGGTGTCCTTAAAC | 25 |
| Tie2 | R | TCCGCAGGGCAGTCAATTC | 26 |
| Tnnt2 | F | GCGGAAGAGTGGGAAGAGACA | 27 |
| Tnnt2 | R | CCACAGCTCCTTGGCCTTCT | 28 |
| VE-cadherin | F | TGGCTTGTCGAATTTGAAGCA | 29 |
| VE-cadherin | R | TCTGGTGAGTGGGTTAGAGGCTATC | 30 |

The above real-time PCR was performed in order to compare expression levels of NKX2.5, Gata4 and MEF2c, which are cardiomyocyte-specific genes among the groups of mouse cardiomyocytes (H), mouse embryonic fibroblasts (MEF), and mouse embryonic fibroblasts treated with exosomes and chemical agents for inducing cardiomyocyte differentiation (iCM).

Figure 9:
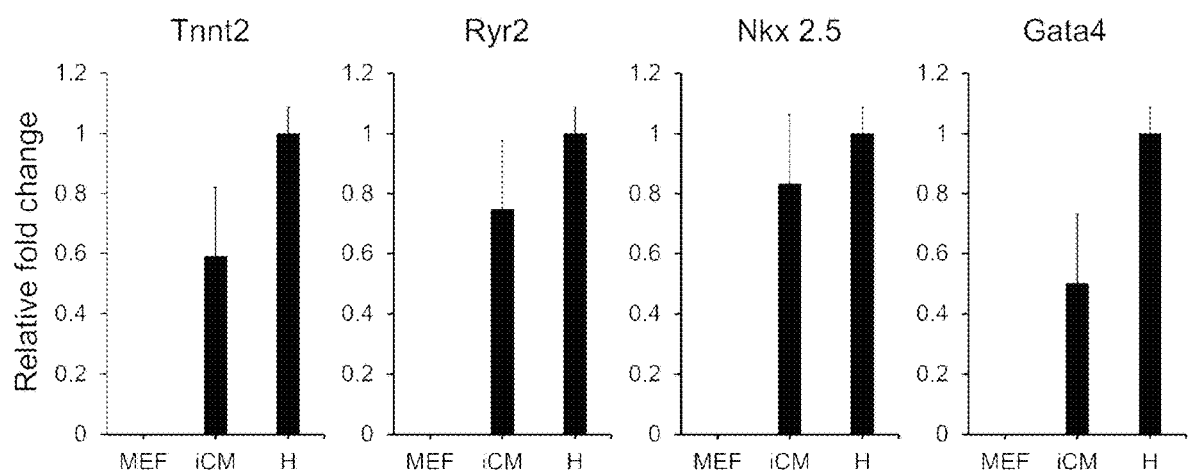
FIG. 9 is a series of graphs showing the expression of Tnnt2, Ryr2, Nkx2.5, and Gata4, which are specific genes of mouse myocardial cells through quantitative real time PCR, in mouse embryonic fibroblasts (MEF), induced cardiomyocyte (iCM) prepared by treating fibroblasts with exosomes derived from stem cells and a chemical agent for inducing cardiomyocytes, and mouse cardiomycytes (H).

As a result, as shown in FIG. 9, it was confirmed that increase in the expression of cardiac-specific genes, including Tnnt2, Ryr2, Nkx2.5, and Gata4, compared with control MEF.

Example 6: Next-Generation Sequencing of iCMs and Exosomes

Quantseq 3' mRNA sequencing was performed for gene expression analysis of cells, and miRNA sequencing was carried out for exosome analysis. The beating colonies were picked at designated day and total RNA was isolated using Trizol reagent (Thermo Scientific Inc). RNA quality was assessed by Agilent 2100 bioanalyzer using the RNA 6000 Nano Chip for Quantseq 3' mRNA sequencing and the RNA 6000 Pico Chip for exosomal miRNA sequencing (both from Agilent Technologies). RNA quantification was performed using a NanoDrop 2000 Spectrophotometer system (Thermo Scientific). For the construction of library, QuantSeq 3' mRNA-Seq Library Prep Kit (Lexogen, Inc., Austria) was used for gene expression analysis, and NEBNext® Multiplex Small RNA Library Prep kit (New England BioLabs) was used for exosomal miRNA sequencing according to the manufacturer's instructions. The yield and size distribution of the small RNA libraries were assessed by the Agilent 2100 Bioanalyzer instrument for the High-sensitivity DNA Assay (Agilent Technologies) and high-throughput sequences were produced by NextSeq™ 500 system as way of single-end 75 sequencing (Illumina). Sequence reads were mapped by Bowtie2 software tool in order to obtain bam file (alignment file). Read counts mapped on differentially expressed gene and mature miRNA sequence were extracted from the alignment file using Bedtools (v2.25.0) and Bioconductor that uses R (version 3.2.2) statistical programming language (R development Core Team, 2016). Read counts were used in order to determine the expression level of miRNAs. Quantile normalization method was used for comparison between samples. Gene classification was based on searches done by DAVID (http://david.abcc.ncifcrf.gov/) and Medline databases (http://www.ncbi.nlm.nih.gov/). For miRNA target study, miRWalk 2.0 was performed. Hierarchical cluster analyses were carried out with Euclidean distance correlation as the distance measurement with average linkage. Clusters and heat maps were visualized via MeV 4.9.0.

Figure 10:
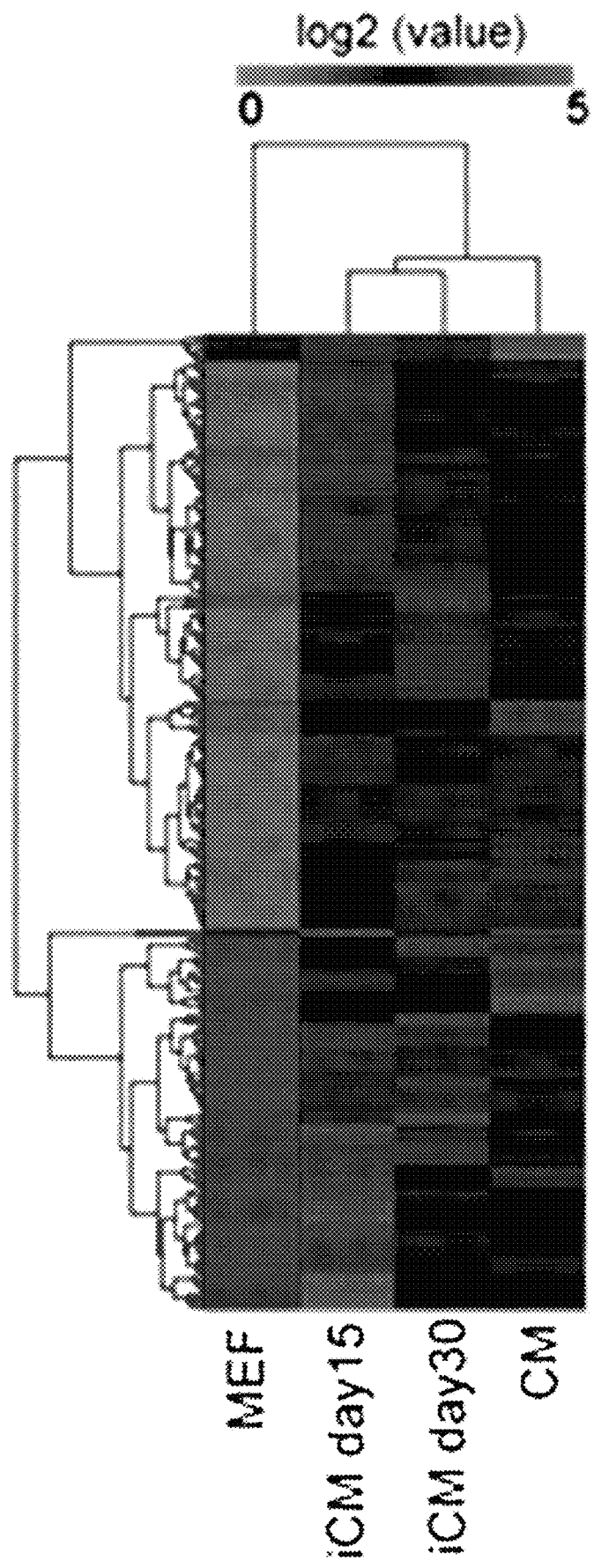
FIG. 10 represents a gene expression profile showing gene expression in mouse embryonic fibroblast (MEF), induced cardiomyocyte (iCM, day 15 and 30) and cardiomyocyte (CM) analyzed by Qunatseq 3' mRNA sequencing. Showed up to 5-fold more up-regulated or down-regulated genes in iCM compared to MEF. It was confirmed that iCM shared similar gene expression profiles with nCM.

As shown in FIG. 10, the global gene expression of MEF, iCM (day 15, 30) and cardiomyocyte were analyzed by Quantseq 3' mRNA sequencing. Compared with MEF, the patterns of genes that were highly expressed and less expressed in iCM were very similar to the cardiomyocyte group.

Figure 11:
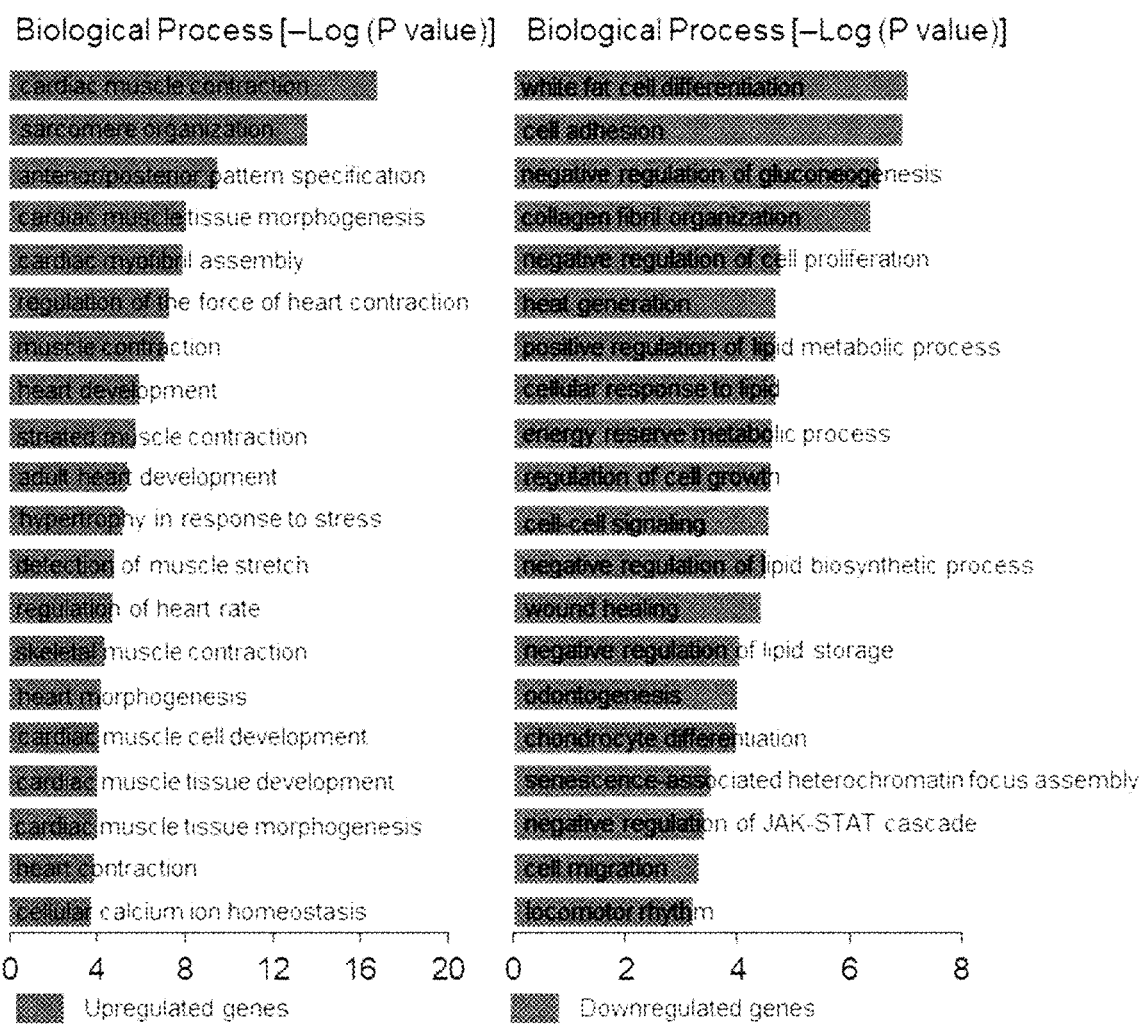
FIG. 11 is a series of graphs representing gene ontology (GO) term enrichment analysis of genes that display >5-fold change in expression in iCM compared with MEF. Left, upregulated genes; right, downregulated genes. GO terms were defined as cardiac contraction, sarcomere organization and cardiac development.

In addition, as shown in FIG. 11, gene ontology (GO) term enrichment analysis showed that upregulated genes are involved in heart contraction, sarcomere organization and heart development.

Figure 12:
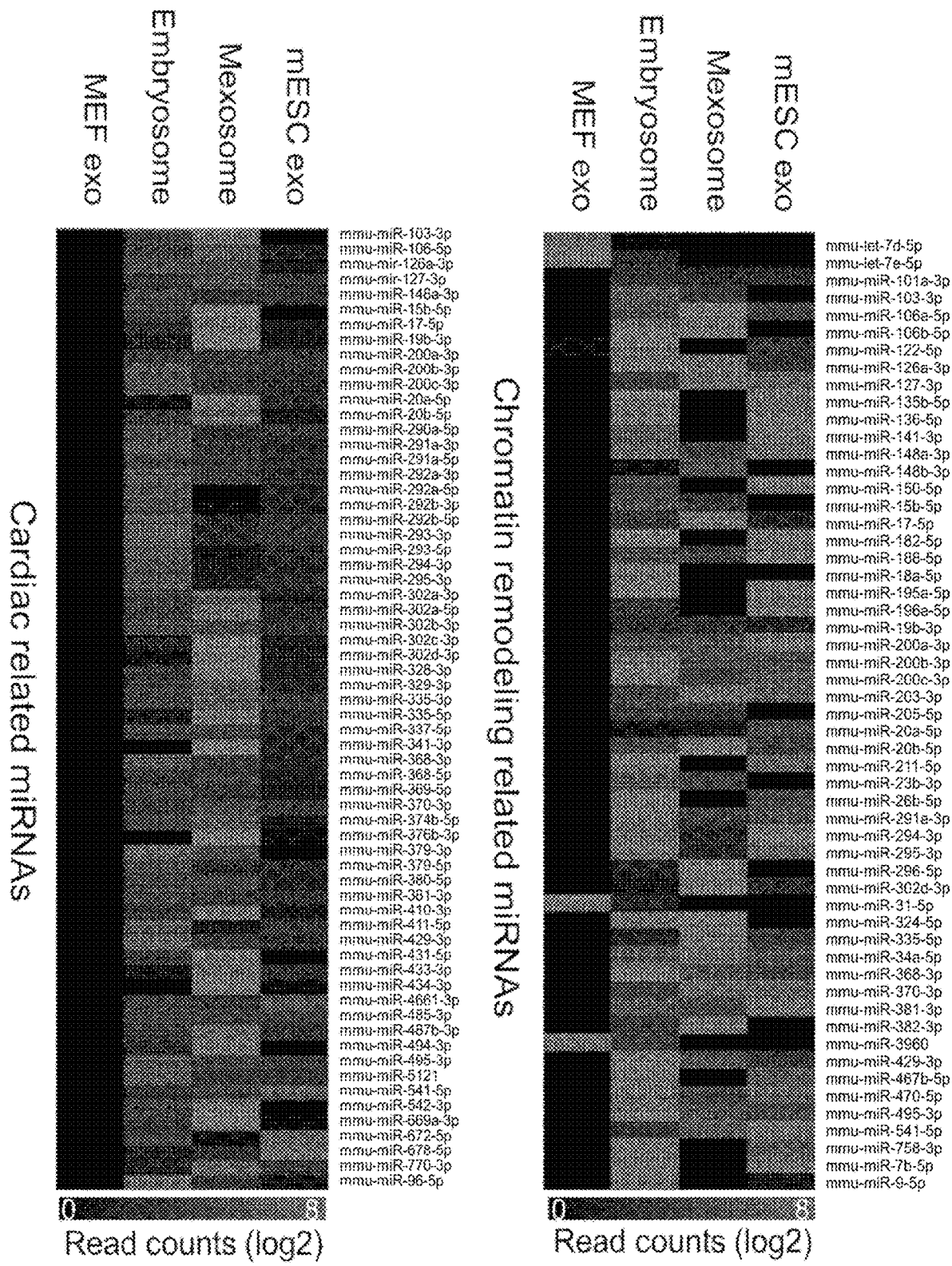
FIG. 12 represents Heatmaps of chromatin remodeling related miRNAs and cardiogenesis related miRNAs from MEF-exosomes, embryosomes, mexosomes, and mESC-exosomes. A miRNA target gene was analyzed by public database searching and gene ontology (GO) analysis.
Figure 14:
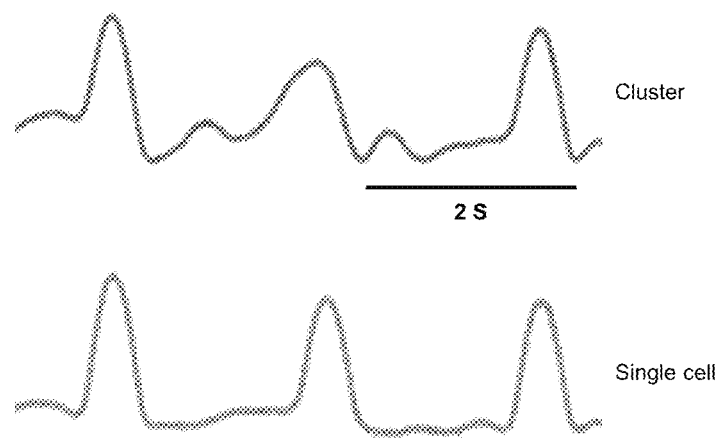
FIG. 14 is a series of graph representing Calcium flux in iCMs at day 25 after induction. Traces of calcium transients of one cluster (upper) and single cell (lower). It is confirmed that the mean peak amplitude of [$Ca^{2+}$] (peak fluorescence intensity ratio, $\Delta F/F0$) in iCMs was 3.14±0.02 (n=6), similar to those shown in neonatal or ESC-derived cardiomyocytes.

Further, as shown in FIG. 12, miRNA target gene analysis by public database searching, and gene ontology (GO) analysis revealed that a number of miRNAs in embryosome and mexosome were associated with chromatin remodeling and cardiac development.

In addition, as shown in FIG. 13, miRNA expression levels were calculated using read counts, miRNAs with higher expression levels in embryosome and mexosome than MEF and ESC-derived exosomes were investigated. The expression levels of miR-290 cluster, miR-302-367 cluster and miR-200, which are involved in pluripotency, mesoderm induction and somatic reprogramming, respectively, was high in the embryosome, and the expression level of miR-1, which has a great effect on cardiac development, was high in the mexosome.

Example 8: Intracellular $Ca^{2+}$ Measurement

To record calcium transients, the induced cardiomyocytes (iCMs) were loaded with 2 μM Fluo-3 AM $Ca^{2+}$ indicator (Thermo Scientific), as directed by the manufacturer, at 37° C. for 20 min to allow for de-esterification of the dye. After removing remain dye in the media by changing media, spontaneous $Ca^{2+}$ transients were recorded at 37° C. using BX51 Fluorescence Microscope (Olympus) and a time-lapse recording system (Xcellence). For clusters of cardiomyocytes, cell-framing adapters were adjusted to record fluorescence for whole clusters and cell-free boundaries and background fluorescence was recorded after cells were removed from the field of view at the end for normalization.

As shown in FIG. 13, the peak fluorescence intensity ratio (F/FO) in these transients was 3.14±0.02 (n=6), similar to previous measurements made using neonatal or embryonic stem cell-derived cardiomyocytes.

Example 9: Electrophysiological Analysis

Conventional whole-cell patch clamp was performed. Spontaneously beating induced cardiomyocytes (iCMs) were selected to record action potential (AP). iCMs were perfused at physiological temperature 35-37° C. with normal Tyrode's solution contained 145 mM NaCl, 5.4 mM KCl, 1 mM $MgCl_2$, 1.8 mM $CaCl_2$, 10 mM HEPES and 5 mM glucose, adjusted to pH 7.4 with NaOH. Intracellular pipette solution contained 120 mM K-Aspartate, 25 mM KCl, 5 mM NaCl, 10 mM HEPES, 0.1 mM EGTA, 1 mM $MgCl_2$, 3 mM Mg-ATP, adjusted pH 7.2 with KOH. Liquid junction potential compensation (10 mV) was applied after the experiment. Micro-glass patch pipettes (World Precision Instruments) were pulled by PP-830 puller (Narishige, Japan) with resistance between 2-3 MΩ. Axopatch 200B amplifier, Digidata 1550B AD-DA convertor and pClamp software 11 (Axon Instruments) were used for AP recording and analysis.

| Cell Type | APA (mV) | dv/dtMax (V/s) | Freq (Hz) | MDP (mV) | APD90 (ms) |
|---|---|---|---|---|---|
| V-like (n = 10) | 87.3 ± 5.9 | 48.8 ± 9.5 | 1.6 ± 0.3 | −73.9 ± 2.7 | 59.6 ± 21.0 |
| A-like (n = 4) | 81.1 ± 5.3 | 40.6 ± 15.8 | 2.6 ± 0.9 | −69.8 ± 4.1 | 49.3 ± 10.2 |

As shown in Table 3, the action potentials (AP) were analyzed using the patch clamp technique, and many iCMs showed ventricular-like AP morphology with a mean diastolic potential (MDP) of −73.9 mV.

Collectively, it was confirmed that direct reprogramming of fibroblasts into cardiomyocytes could be achieved safely through bio-derived exosomes and cardiomyocyte-inducing chemical agents without transfection through non-viral vectors or viral infection.

In conclusion, the exosome-based myocardial cell cross-differentiation induction method of the present invention treats somatic cells with a composition containing a biocompatible non-viral exosome and a cardiomyocyte inducing drug. Thus, it is possible to directly induce myocardial cells from somatic cells, thereby securing the safety of the body without worry of viral infection or mutation of inherent genes in somatic cells. Therefore, it can be utilized as a new concept of in vivo cell therapy platform technology for treating heart disease.

While the present invention has been described with reference to examples and experimental examples, it is to be understood that the invention is not limited to the disclosed exemplary examples, and on skilled in the art may comprehend that there are various modifications and equivalent examples. Accordingly, the true scope of the present invention should be determined by the technical idea of the appended claims.

What is claimed is:

1. An in vitro method of inducing trans-differentiation of a fibroblast to a cardiomyocyte, the method comprising:
   a) isolating first exosomes isolated from stem cells during a mesoderm induction process and second exosomes isolated from the stem cells during a cardiac specification and maturation process;
   b) culturing a fibroblast in a cardiomyocyte reprogramming medium containing the first exosomes; and
   c) culturing the fibroblast in a cardiomyocyte differentiation medium containing the second exosomes isolated from the step a);
   wherein the first exosomes comprise miR-291a-3p, miR-292a-3p, miR-292a-5p, miR-293-3p, miR-293-5p, miR-295-3p, miR-294-3p, miR-292b-5p, miR-148a-3p, miR-363-3p, miR429-3p, miR291a-5p, miR-200b-3p, miR-672-5p, miR-335-3p, miR-302b-3p, miR-200a-5p, miR-881-3p, and miR-135b-5p, and the expression of miR-291a-3p, miR-292a-3p and miR-292a-5p is more than twice that of the fibroblast;
   wherein the second exosomes comprise miR-1a-3p, miR-302d-3p, miR-292a-3p, miR-291a-ep, miR-302c-3p, miR-335-3p, miR-431-5p, miR-376b-3p, miR-434-3p, miR-1b-5p, miR-434-3p, miR-293-3p, miR-291a-5p, miR-302b-3p, miR-126a-5p, miR-355-5p, miR-126b-3p, miR-148a-3p, miR-292b-3p, miR-292a-5p and miR-363-3p, and the expression of miR-1a-3p and miR-302d-3p is more than twice that of the fibroblast; and
   wherein the fibroblast is isolated from the same species as the stem cells.

2. The method according to claim 1, wherein a mixing ratio of the first exosomes and the second exosomes is from 1:19 to 19:1.

3. The method according to claim 1, the cardiomyocyte differentiation medium comprises 12 to 20 wt % of fetal bovine serum, 20 to 70 μg/ml of ascorbic acid, 0.5 to 2 μg/ml of insulin, and 500 to 1,500 units/ml of leukemia inhibitory factor actor.

4. The method according to claim 3, wherein the cardiomyocyte differentiation medium further comprises a chemical agent for inducing cardiomyocyte differentiation.

5. The method according to claim 4, wherein the chemical agent is one or a mixture of two or more selected from the group consisting of CHIR99021, PD0325901, SB431542, Tranylcypromine, Forskolin, Repsox, TTNPB, and Valproic Acid (VPA).

6. The method according to claim 5, wherein the chemical agent is added to the cardiomyocyte differentiation medium at a concentration of 1 to 50 μM.

7. An in vitro method for trans-differentiating a fibroblast into a cardiomyocyte, comprising:

a) isolating exosomes in a culture medium during a process of differentiating stem cells into cardiomyocytes, wherein the exosomes are prepared by mixing first exosomes isolated from the stem cells during a mesoderm induction process and second exosomes isolated from the stem cells during a cardiac specification and maturation process;

b) culturing the fibroblast in a cardiomyocyte reprogramming medium containing the exosomes isolated in the step a); and c) culturing the fibroblast in a cardiomyocyte differentiation medium containing the exosomes isolated in the step a) and a chemical agent for inducing cardiomyocyte differentiation;

wherein the first exosomes comprise miR-291a-3p, miR-292a-3p, miR-292a-5p, miR-293-3p, miR-293-5p, miR-295-3p, miR-294-3p, miR-292b-5p, miR-148a-3p, miR-363-3p, miR429-3p, miR291a-5p, miR-200b-3p, miR-672-5p, miR-335-3p, miR-302b-3p, miR-200a-5p, miR-881-3p, and miR-135b-5p, and the expression of miR-291a-3p, miR-292a-3p and miR-292a-5p is more than twice that of the fibroblast;

wherein the second exosomes comprise miR-1a-3p, miR-302d-3p, miR-292a-3p, miR-291a-ep, miR-302c-3p, miR-335-3p, miR-431-5p, miR-376b-3p, miR-434-3p, miR-1b-5p, miR-434-3p, miR-293-3p, miR-291a-5p, miR-302b-3p, miR-126a-5p, miR-355-5p, miR-126b-3p, miR-148a-3p, miR-292b-3p, miR-292a-5p and miR-363-3p, and the expression of miR-1a-3p and miR-302d-3p is more than twice that of the fibroblast; and wherein the fibroblast is isolated from the same species as the stem cells.

8. A composition for inducing trans-differentiation of a fibroblast into a cardiomyocyte comprising first exosomes isolated from stem cells during a mesoderm induction process, and second exosomes isolated during a cardiac specification and maturation process in the differentiation of stem cells into cardiomyocytes, and a chemical agent for inducing cardiomyocyte differentiation, wherein the chemical agent is a mixture of CHIR99021 and PD0325901;

wherein the first exosomes comprise miR-291a-3p, miR-292a-3p, miR-292a-5p, miR-293-3p, miR-293-5p, miR-295-3p, miR-294-3p, miR-292b-5p, miR-148a-3p, miR-363-3p, miR429-3p, miR291a-5p, miR-200b-3p, miR-672-5p, miR-335-3p, miR-302b-3p, miR-200a-5p, miR-881-3p, and miR-135b-5p, and the expression of miR-291a-3p, miR-292a-3p and miR-292a-5p is more than twice that of the fibroblast;

wherein the second exosomes comprise miR-1a-3p, miR-302d-3p, miR-292a-3p, miR-291a-ep, miR-302c-3p, miR-335-3p, miR-431-5p, miR-376b-3p, miR-434-3p, miR-1b-5p, miR-434-3p, miR-293-3p, miR-291a-5p, miR-302b-3p, miR-126a-5p, miR-355-5p, miR-126b-3p, miR-148a-3p, miR-292b-3p, miR-292a-5p and miR-363-3p, and the expression of miR-1a-3p and miR-302d-3p is more than twice that of the fibroblast;

wherein the fibroblast is isolated from the same species as the stem cells; and wherein a mixing ratio of the first exosomes and the second exosomes is from 1:19 to 19:1.

\* \* \* \* \*